US012799109B2

(12) United States Patent
Frenkel

(10) Patent No.: US 12,799,109 B2
(45) Date of Patent: Nov. 17, 2026

(54) SALT FORMS OF SABCOMELINE

(71) Applicant: Syremis Therapeutics, Ltd., Petach Tikva (IL)

(72) Inventor: Anton Frenkel, Petach Tikva (IL)

(73) Assignee: Syremis Therapeutics, Ltd., Petach Tikva (IL)

( * ) Notice: Subject to any disclaimer, the term of this patent is extended or adjusted under 35 U.S.C. 154(b) by 0 days.

(21) Appl. No.: 19/419,278

(22) Filed: Dec. 15, 2025

(65) Prior Publication Data

US 2026/0116876 A1 Apr. 30, 2026

Related U.S. Application Data

(63) Continuation of application No. PCT/IB2025/056897, filed on Jul. 8, 2025.

(60) Provisional application No. 63/668,866, filed on Jul. 9, 2024, provisional application No. 63/772,936, filed on Mar. 17, 2025.

(51) Int. Cl.

| | |
|---|---|
| ***C07D 453/02*** | (2006.01) |
| ***A61K 31/439*** | (2006.01) |
| ***C07C 53/126*** | (2006.01) |

(52) U.S. Cl.

CPC .......... *C07D 453/02* (2013.01); *A61K 31/439* (2013.01); *C07C 53/126* (2013.01); *C07B 2200/13* (2013.01)

(58) Field of Classification Search

CPC ............................ C07D 453/02; A61K 31/439

USPC .......................................... 546/133; 514/305

See application file for complete search history.

(56) References Cited

U.S. PATENT DOCUMENTS

| | | | |
|---|---|---|---|
| 5,278,170 | A | 1/1994 | Orlek et al. |
| 5,314,901 | A | 5/1994 | Bromidge et al. |
| 5,356,914 | A | 10/1994 | Bromidge et al. |
| 5,362,739 | A | 11/1994 | Orlek et al. |
| 5,545,740 | A | 8/1996 | Hughes et al. |
| RE35,593 | E | 8/1997 | Orlek et al. |
| 5,675,007 | A | 10/1997 | Keogh et al. |
| 5,773,619 | A | 6/1998 | Bromidge et al. |
| 5,808,075 | A | 9/1998 | Bromidge et al. |
| 6,451,343 | B1 | 9/2002 | Glinecke et al. |
| 6,468,560 | B2 | 10/2002 | Sauer et al. |
| 2001/0018074 | A1 | 8/2001 | Napper et al. |
| 2002/0127271 | A1 | 9/2002 | Van-Schie et al. |
| 2008/0081804 | A1 | 4/2008 | Routledge et al. |
| 2009/0306040 | A1 | 12/2009 | Sharpe et al. |

FOREIGN PATENT DOCUMENTS

| | | | |
|---|---|---|---|
| EP | 392803 B1 | 10/1990 | |
| WO | 2016205071 | 12/2016 | |
| WO | WO 2026-013573 A1 * | 1/2026 | .......... C07D 453/02 |

OTHER PUBLICATIONS

Berge et al., "Pharmaceutical Salts", J Pharmaceutical Sciences, 1977, 66(1), 1-19.

Bromidge et al., "A Novel and Selective Class of Azabicyclic Muscarinic Agonists Incorporating An N-Methoxy Imidoyl Halide or Nitrile Functionality", Biorganic & Medicinal Chemistry Letters, 1992, 2(8), 791-796.

Bromidge et al., "Synthesis and Properties of [R-(Z)]-+( )-α-I(-A zabicyclo[2.2.2]oct-3-yl)-α-(methoxyimino)acetonitrile, a Novel Functionally Selective Muscarinic Partial Agonist", J Chem Soc Chem Commun, 1994, 2189-2190.

Bromidge et al., "Design of [R-(Z)]-(+)-α-(Methoxyimino)-1-azabicyclo[2.2.2]octane-3-acetonitrile (SB 202026), a Functionally Selective Azabicyclic Muscarinic M1 Agonist Incorporating the N-Methoxy Imidoyl Nitrile Group as a Novel Ester Bioisostere", J Med Chem, 1997, 40(26), 4265-4280.

De La Peña-Gil et al., "Simplifying Hansen Solubility Parameters for Complex Edible Fats and Oils", Food Biophysics, 2016, 11, 283-291.

Florence et al., "The Solid State" Modern Pharmaceutics, Chapter 8, 5th ed., vol. 1, Basic Principles and Systems, Informa Healthcare, USA, Inc, Jan. 1, 2010, 253-310.

Gould P, "Salt selection for basic drugs", Int J Pharm, 1986, 33, 201-207.

Gupta et al., "Salts of Therapeutic Agents: Chemical, Physicochemical, and Biological Considerations", Molecules 2018, 23, 1719.

Hansen C, "Hansen Solubility Parameters, A User's Handbook", CRC Press, 2nd Ed, 2007, 1-546.

Holm et al., "Long-Acting Injectable Aqueous Suspensions-Summary From an AAPS Workshop", The AAPS Journal, 2023, 25, 49.

Nkanga et al., "Clinically established biodegradable long acting injectables: An industry perspective", Advanced Drug Delivery Systems, 2020, 167, 19-46.

Paulekhun et al., "Trends in Active Pharmaceutical Ingredient Salt Selection Based on Analysis of the Orange Book Database", J Med Chem, 2007, 50, 6665-6672.

"Sabcomeline Hydrochloride" Drugs of the Future, 1998, 23(1), 41-44.

Stahl et al., "Handbook of Pharmaceutical Salts, Properties, Selection and Uses", Wiley-VCH, 2002, 1-364.

Stefanis et al., "Prediction of Hansen Solubility Parameters with a New Group-Contribution Method", Int J Thermophys, 2008, 29, 568-585.

Veerbeeck et al., "Generic substitution: The use of medicinal products containing different salts and implications for safety and efficacy", Eur J Pharm Sci, 2006, 1-6.

Wright et al, "Long-Acting Implants and Injections", Springer, 2012, 1-556.

International Search Report and Written Opinion for PCT/IB2025/056914 dated Sep. 29, 2025.

(Continued)

*Primary Examiner* — Charanjit Aulakh

(74) *Attorney, Agent, or Firm* — FLOREK & ENDRES PLLC

(57) ABSTRACT

The invention relates to the stearate salt of sabcomeline. The stearate salt of sabcomeline may be a solid, preferably in a crystalline solid. The invention also relates to various polymorphic forms of sabcomeline stearate salt. The invention further relates to methods of preparing the stearate salt of sabcomeline and its various polymorphic forms and to pharmaceutical compositions containing the stearate salt of sabcomeline and its various polymorphic forms.

4 Claims, 5 Drawing Sheets

(56) References Cited

OTHER PUBLICATIONS

International Search Report and Written Opinion for PCT/IB2025/056897 dated Aug. 25, 2025.
International Search Report and Written Opinion for PCT/IB2025/056903 dated Aug. 27, 2025.
International Search Report and Written Opinion for PCT/IB2025/056909 dated Sep. 29, 2025.
Haynes et al., "Occurrence of Pharmaceutically Acceptable Anion and Cations in the Cambridge Structural Database," Journal of Pharmaceutical Sciences, vol. 94, No. 10, Oct. 2005 pp. 211-2120.
U.S. Appl. No. 19/419,341 Office Action dated Feb. 25, 2026.
U.S. Appl. No. 19/419,305 Office Action dated Mar. 12, 2026.

* cited by examiner

SALT FORMS OF SABCOMELINE

CROSS-REFERENCE TO RELATED APPLICATIONS

This application is a continuation of International Patent Application No. PCT/IB2025/056897 filed on Jul. 8, 2025 which claims the benefits of U.S. Provisional Application Ser. No. 63/668,866, as filed on Jul. 9, 2024, and U.S. Provisional Application Ser. No. 63/772,936, as filed on Mar. 17, 2025, the disclosures of which are incorporated herein by reference in their entirety.

BACKGROUND TO THE INVENTION

Sabcomeline is an M1/M4 muscarinic agonist. Development of its hydrochloride salt form was halted in the late 1990s after the product failed in Phase III studies in the symptomatic treatment of Alzheimer's disease.

Methods of manufacturing the compound and its oxalate salt are described in EP392803. A method of manufacturing sabcomeline hydrochloride from sabcomeline base is described in WO9531456. Sabcomeline HCl is also described in WO9810762 as having very high water solubility. Few other details of the compound's chemical properties are known.

Different salts of a drug may possess different properties. For example, different salts may have different processing or handling characteristics, different dissolution profiles, different stabilities, or different shelf-lives. These variations in the properties of different salts may impact the final dosage form, for instance, if they affect bioavailability. Different salts of a drug may also give rise to a variety of polymorphs, which may in turn have unique properties.

Polymorphism, the occurrence of different crystal forms, is a property of some molecules and molecular complexes. A single compound, like sabcomeline, may give rise to a variety of polymorphs having distinct crystal structures and physical properties like melting point, thermal behaviors (e.g. measured by thermogravimetric analysis—"TGA", or differential scanning calorimetry—"DSC"), X-ray powder diffraction (XRPD) pattern, infrared absorption fingerprint, Raman absorption fingerprint, and solid state (13C-) NMR spectrum. One or more of these techniques may be used to distinguish different polymorphic forms of a compound.

New salts and solid-state forms and solvates of a drug substance can exhibit different properties, such as differences in handling, processing, storage, and purification. In some cases, intermediate solid forms may convert to other salts or polymorphic forms. New polymorphic forms and solvates of a pharmaceutically useful compound can also change performance characteristics of a pharmaceutical product (dissolution profile, bioavailability, etc.). This large repertoire of materials creates challenges for scientists, as products having surprisingly different properties can arise just by a change in salt or polymorphic form. Improved solid forms of sabcomeline are needed.

SUMMARY OF THE INVENTION

The present invention relates to sabcomeline stearate and solid-state forms thereof. In a preferred embodiment, the present invention relates to sabcomeline stearate Form III.

The present invention further encompasses the use of the above-described salt and solid-state forms thereof, for the preparation of other solid-state forms of sabcomeline stearate, other sabcomeline salts and their solid-state forms thereof.

The present invention further encompasses compositions comprising sabcomeline stearate, and solid-state forms thereof, and their preparation. In some embodiments, the composition is a pharmaceutical composition.

The present invention further encompasses pharmaceutical compositions comprising sabcomeline stearate, and solid-state forms thereof, and their preparation.

In one embodiment, the present invention encompasses processes for preparing said pharmaceutical formulation comprising combining sabcomeline stearate and solid-state forms thereof, and at least one pharmaceutically acceptable excipient.

BRIEF DESCRIPTION OF THE DRAWINGS

FIG. 1 shows an X-ray powder diffraction (XRPD) pattern of Form I of sabcomeline oxalate prepared according to Example 4a.

DETAILED DESCRIPTION OF THE INVENTION

Figure 1:
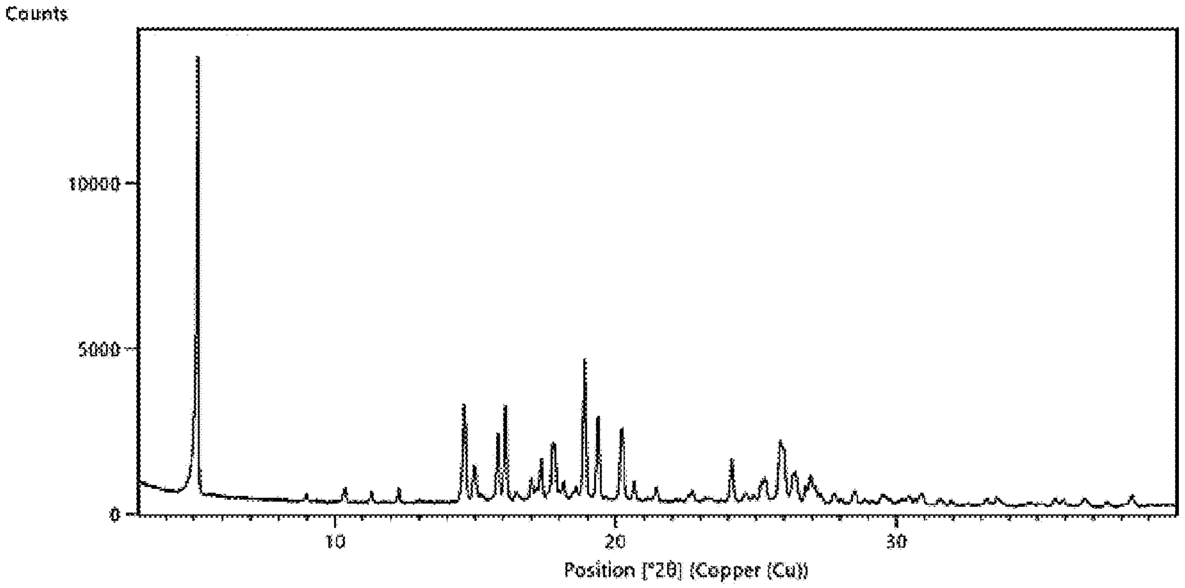

The present inventions may be understood more readily by reference to the following detailed description taken in connection with any accompanying figures and examples, which form a part of this disclosure. It is to be understood that these inventions are not limited to the specific products, methods, conditions or parameters described and/or shown herein, and that the terminology used herein is for the purpose of describing particular embodiments by way of example only and is not intended to be limiting of the claimed inventions.

The entire disclosures of each patent, patent application, and publication cited or described in this document are hereby incorporated herein by reference.

As employed above and throughout the disclosure, the following terms and abbreviations, unless otherwise indicated, shall be understood to have the following meanings.

In the present disclosure the singular forms "a", "an", and "the" include the plural reference, and reference to a particular numerical value includes at least that particular value, unless the context clearly indicates otherwise. Thus, for example, a reference to "a particle" is a reference to one or more of such particles and equivalents thereof known to those skilled in the art, and so forth. Furthermore, when indicating that a certain element "may be" X, Y, or Z, it is not intended by such usage to exclude in all instances other choices for the element.

When values are expressed as approximations, by use of the antecedent "about", it will be understood that the particular value forms another embodiment. As used herein, "about X" (where X is a numerical value) preferably refers to ±10% of the recited value, inclusive. For example, the phrase "about 8" preferably refers to a value of 7.2 to 8.8, inclusive; as another example, the phrase "about 8%" preferably refers to a value of 7.2% to 8.8%, inclusive. Where present, all ranges are inclusive and combinable. For example, when a range of "1 to 5" is recited, the recited range should be construed as optionally including ranges "1 to 4", "1 to 3", "1-2", "1-2 & 4-5", "1-3 & 5", and the like. In addition, when a list of alternatives is positively provided, such a listing can also include embodiments where any of the alternatives may be excluded. For example, when a range of "1 to 5" is described, such a description can support situations whereby any of 1, 2, 3, 4, or 5 are excluded: thus, a recitation of "1 to 5" may support "1 and 3-5, but not 2", or simply "wherein 2 is not included". The phrase "at least about x" is intended to embrace both "about x" and "at least x". It is also understood that where a parameter range is provided, all integers within that range, and tenths thereof, are also provided by the invention. For example, "2-5 hours" includes 2 hours, 2.1 hours, 2.2 hours, 2.3 hours etc. up to 5 hours.

As used herein, the term "sabcomeline" shall refer to the chemical compound α-(Methoxyimino)-1-azabicyclo[2.2.2]octane-3-acetonitrile and stereoisomers thereof. Sabcomeline includes one chiral center and can exist as two enantiomers, R and S. Sabcomeline includes one imine bond, which can exist in two geometries, Z and E.

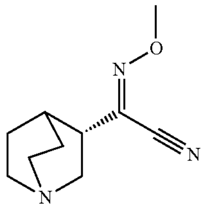

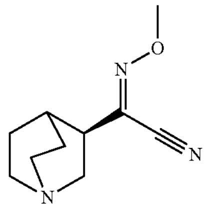

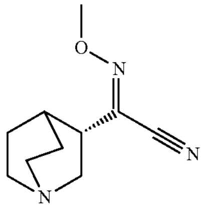

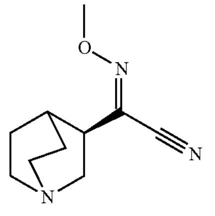

According to the disclosure, sabcomeline can be present as a single isomer or as a mixture of two, three, or four isomers. Sabcomeline isomer mixtures can include the two, three, or four isomers in any molar amount.

In one embodiment of the invention, sabcomeline is racemic (αZ)-α-(Methoxyimino)-1-azabicyclo[2.2.2]octane-3-acetonitrile. In another embodiment of the invention, sabcomeline is an isomeric mixture of (3R)-α-(Methoxyimino)-1-azabicyclo[2.2.2]octane-3-acetonitrile. In another embodiment of the invention, sabcomeline is enantiomerically pure (αZ,3R)-α-(Methoxyimino)-1-azabicyclo[2.2.2]octane-3-acetonitrile:

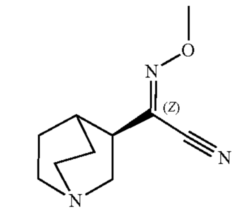

As used herein, the term "stereoisomer" corresponds to a compound where the same atoms or isotopes connected by bonds of the same type differ in their relative positions in space.

As used herein, the term "racemic" corresponds to a compound comprising a homogeneous phase composed of equimolar amounts of enantiomeric molecules. It is also contemplated that a racemic compound might also contain geometric bonds such as cis and trans-forms of the compound. In one embodiment of the invention, these geometric isomers will be in equimolar amounts within the compound. In another embodiment of the invention, one geometric isomer will be in excess of any other within the compound. In one embodiment of the invention, a racemic compound could relate to a compound wherein one geometric isomer will comprise at least 50.1% of the compound. In one embodiment of the invention, a racemic compound could relate to a compound wherein one geometric isomer will comprise at least 50.1%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 98.5%, at least 99%, at least 99.1%, at least 99.2%, at least 99.3%, at least 99.4%, at least 99.5%, at least 99.6%, at least 99.7%, at least 99.8% or at least 99.9% of the compound. As an example, a racemic compound containing both chiral and geometric bond could be described without any stereochemical nomenclature wherein no geometric isomer is in excess of any other or by denoting a geometric excess of at least one geometric isomer, e.g., (Z)- or cis-.

As used herein, the term "isomeric mixture" corresponds to a compound comprising a homogeneous phase of equimolar amounts of geometric isomers, that is, equimolar amounts of Z and E geometries. An isomeric mixture might contain (S)- and (R)-enantiomers of the compound, either of which can be present in any molar amount. In one embodiment of the invention, these enantiomers will be in equimolar amounts within the compound. In another embodiment of the invention, one enantiomer will be in excess of any other within the compound. In one embodiment of the invention, an isomeric mixture could relate to a compound wherein one enantiomer will comprise at least 50.1% of the compound. In one embodiment of the invention, an isomeric mixture could relate to a compound wherein one enantiomer will comprise at least 50.1%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 98.5%, at least 99%, at least 99.1%, at least 99.2%, at least 99.3%, at least 99.4%, at least 99.5%, at least 99.6%, at least 99.7%, at least 99.8% or at least 99.9% of the compound. As an example, an isomeric mixture of a compound containing both chiral and geometric bonds could be described without any geometric nomenclature, wherein no geometric isomer is in excess of any other, or by denoting an excess of at least one enantiomer, e.g., an excess of either the (R)- or (S)-enantiomer.

As used herein, the term "enantiomerically pure" corresponds to a compound wherein one stereoisomer is present in excess over all others. For example, an enantiomerically pure form of a compound containing at least one chiral center but not containing any geometric bonds will comprise a single stereoisomer in excess over all other stereoisomeric forms of the compound, whereas an enantiomerically pure form of a compound comprising both chiral and geometric bonds will comprise a single stereoisomer in excess over all other enantiomeric and geometric isomeric forms of the compound. In one embodiment of the invention, an enantiomerically pure compound could relate to a compound wherein one enantiomer will comprise at least 50.1% of the compound. In one embodiment of the invention, an enantiomerically pure compound could relate to a compound wherein one enantiomer will comprise at least 50.1%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 98.5%, at least 99%, at least 99.1%, at least 99.2%, at least 99.3%, at least 99.4%, at least 99.5%, at least 99.6%, at least 99.7%, at least 99.8% or at least 99.9% of the compound. In one embodiment of the invention, an enantiomerically pure compound could relate to a compound comprising only one enantiomer and one geometric isomer will comprise at least 50.1% of the compound. In one embodiment of the invention, an enantiomerically pure compound could relate to a compound comprising only one enantiomer and one geometric isomer will comprise at least 50.1%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 98.5%, at least 99%, at least 99.1%, at least 99.2%, at least 99.3%, at least 99.4%, at least 99.5%, at least 99.6%, at least 99.7%, at least 99.8% or at least 99.9% of the compound. As an example, an enantiomerically pure compound containing single chiral and geometric centers could be denoted by an isomeric excess of both chiral and geometric isomers, e.g., (Z,R)- or cis-(S).

As used herein, the term "sabcomeline stearate" means sabcomeline stearate salt.

As used herein, a crystal form or a crystalline form may be referred to as being characterized by graphical data "as depicted in" a Figure. Such data may include, for example, powder X-ray diffractograms. As is well-known in the art, the graphical data potentially provides additional technical information to further define the respective solid-state form (a so-called "fingerprint") which can not necessarily be described by reference to numerical values or peak positions alone. In any event, the skilled person will understand that such graphical representations of data may be subject to small variations, e.g., in peak relative intensities and peak positions due to factors such as variations in instrument response and variations in sample concentration and purity; which are well known to the skilled person. Nonetheless, the skilled person would readily be capable of comparing the graphical data in the Figures herein with graphical data generated for an unknown crystal form and confirm whether the two sets of graphical data are characterizing the same crystal form or different crystal forms.

Sabcomeline stearate, or crystal forms of sabcomeline stearate as referred to herein, as being characterized by graphical data "as depicted in" a Figure, will thus be understood to include any crystal form of sabcomeline stearate, characterized with the graphical data having such small variations, as are well known to the skilled person, in comparison with the Figure.

As used herein, unless stated otherwise, XRPD peaks reported herein are preferably measured using CuKa radiation, λ=1.5418 A, preferably; XRPD peaks reported herein are measured using Cuk a radiation, λ=1.5418 A, at a temperature of 25±3° C.

A process or step may be referred to herein as being carried out "overnight". This refers to a time interval, e.g., for the process or step, that spans the time during the night, when that process or step may not be actively observed. This time interval is from about 8 to about 20 hours, or about 10 to about 18 hours, typically about 16 hours.

As used herein, and unless stated otherwise, the term "anhydrous" in relation to sabcomeline stearate salt, a crystalline sabcomeline stearate salt or a solid-state form thereof, which does not include any crystalline water (or other solvents) in a defined/non-defined, stoichiometric/non-stoichiometric amount within the crystal. Moreover, an "anhydrous" form does not contain more than about 1% (w/w) of either water or organic solvents as measured for example by thermal gravimetric analysis (TGA).

As used herein, and unless indicated otherwise, the term "solvate" refers to a crystal form that incorporates a solvent in the crystal structure. The solvent in a solvate may be present in either a stoichiometric or in a non-stoichiometric amount.

As used herein, and unless indicated otherwise, the term "isolated" corresponds to sabcomeline stearate salt or solid-state form(s) thereof that is physically separated from the reaction mixture in which it is formed.

The amount of solvent employed in a chemical process, e.g., a reaction or crystallization may be referred to herein as a number of "volumes" or "vol" or "V". For example, a material may be referred to as being suspended in 10 volumes (or 10 vol or 10V) of a solvent. In this context, this expression would be understood to mean milliliters of the solvent per gram of the material being suspended, such that suspending 5 grams of a material in 10 volumes of a solvent means that the solvent is used in an amount of 10 milliliters of the solvent per gram of the material that is being suspended or, in this example, 50 mL of the solvent. In another context, the term "v/v" may be used to indicate the number of volumes of a solvent that are added to a liquid mixture based on the volume of that mixture. For example, adding methyl tert-butyl ether (MTBE) (1.5 v/v) to a 100 ml reaction mixture would indicate that 150 mL of MTBE was added.

As used herein, and unless indicated otherwise the term "non-hygroscopic" in relation to a sabcomeline stearate, or a crystal form thereof, refers to less than about 1.0% (w/w) absorption of water at about 25° C. and about 80% relative humidity (RH) by sabcomeline stearate, or a crystal form thereof, as determined, for example, by TGA. Water can be, for example, atmospheric water.

As used herein, the term "reduced pressure" refers to a pressure that is less than atmospheric pressure, for example, a pressure of about 10 mbar to about 500 mbar.

As used herein, and unless indicated otherwise, the term "thermo-dynamical stability" in relation to sabcomeline stearate and its solid-state forms refers to resistance of the solid-state form to polymorphic conversion under certain conditions, for example, heating, melting or dissolving. In some embodiments, the term refers to less than about 20% (w/w), about 10% (w/w), about 5% (w/w), about 1% (w/w), about 0.5% (w/w), or about 0% (w/w) conversion of a crystal form of sabcomeline stearate to any other solid-state form of sabcomeline, or a salt thereof, as measured by XRPD, over a selected time-period. In some embodiments, the conversion is about 1% (w/w) to about 20% (w/w), about 1% (w/w) to about 10% (w/w), or about 1% (w/w) to about 5% (w/w).

The present invention relates to sabcomeline stearate and to solid state forms thereof, processes for preparation thereof, pharmaceutical compositions and formulations thereof.

In one embodiment, the present invention comprises sabcomeline stearate. The sabcomeline stearate may be isolated, preferably as a solid, and more preferably as a crystalline form.

In one embodiment, the present invention comprises a crystalline sabcomeline stearate exhibiting two, three, four, five, six, seven, eight, nine, ten or more 2θ±0.2° 2θ peaks, each with a relative intensity of more than about 10%, of more than about 15%, of more than about 20%, or of more than about 30%.

Figure 7:
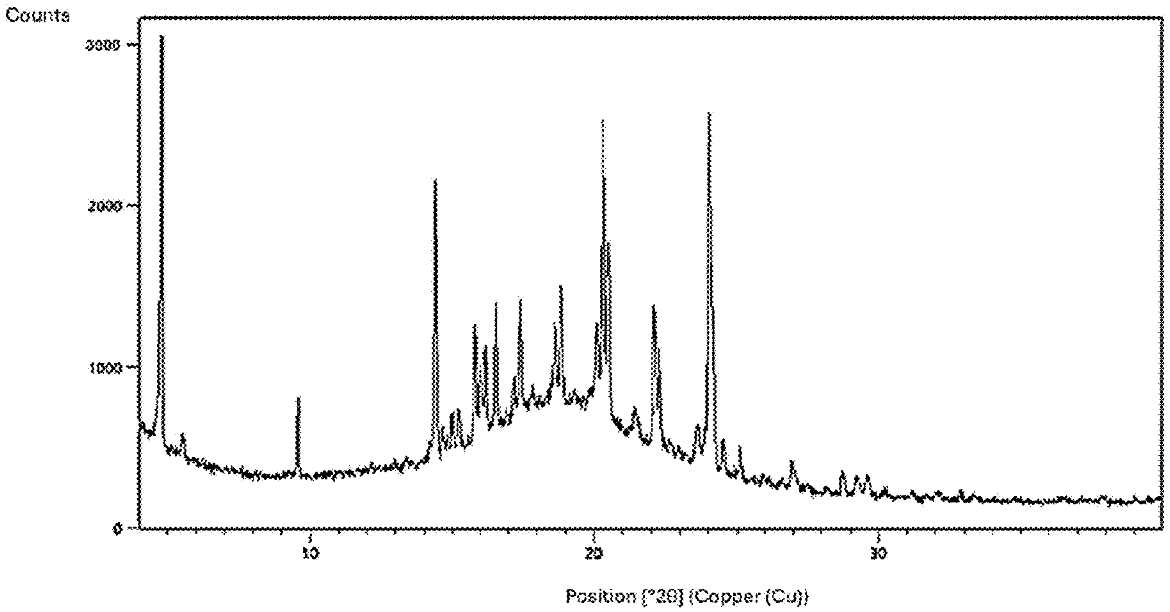
FIG. 7 shows an X-ray powder diffraction (XRPD) pattern of Form I of sabcomeline stearate prepared according to Example 5.
Figure 8:
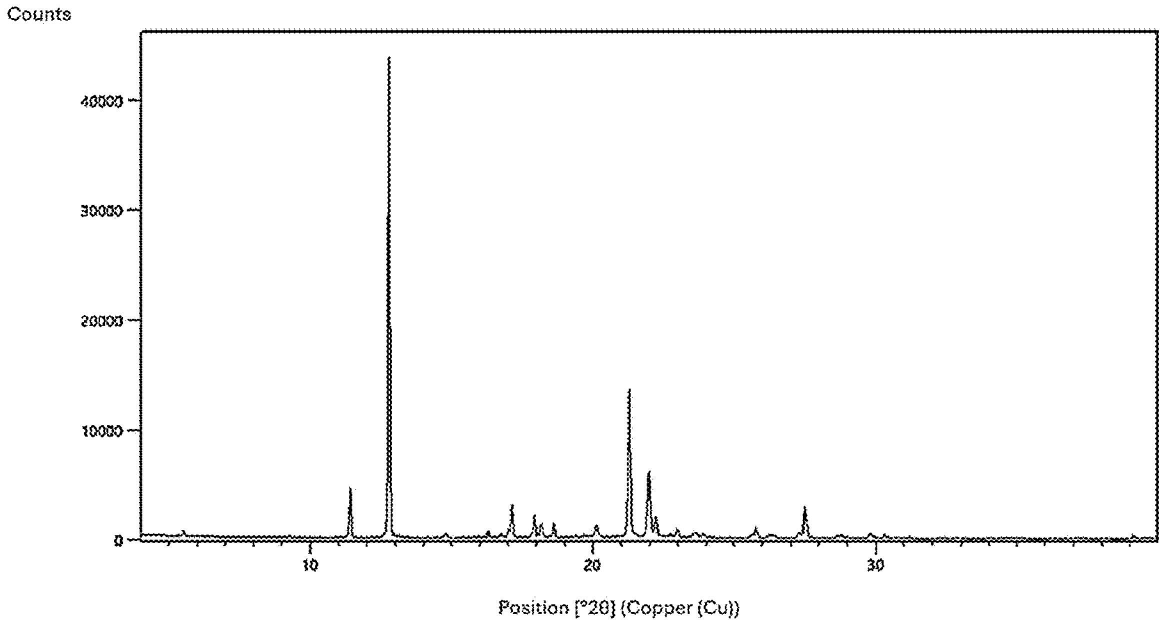
FIG. 8 shows an X-ray powder diffraction (XRPD) pattern of Form II of sabcomeline stearate prepared according to Example 6.
Figure 9:
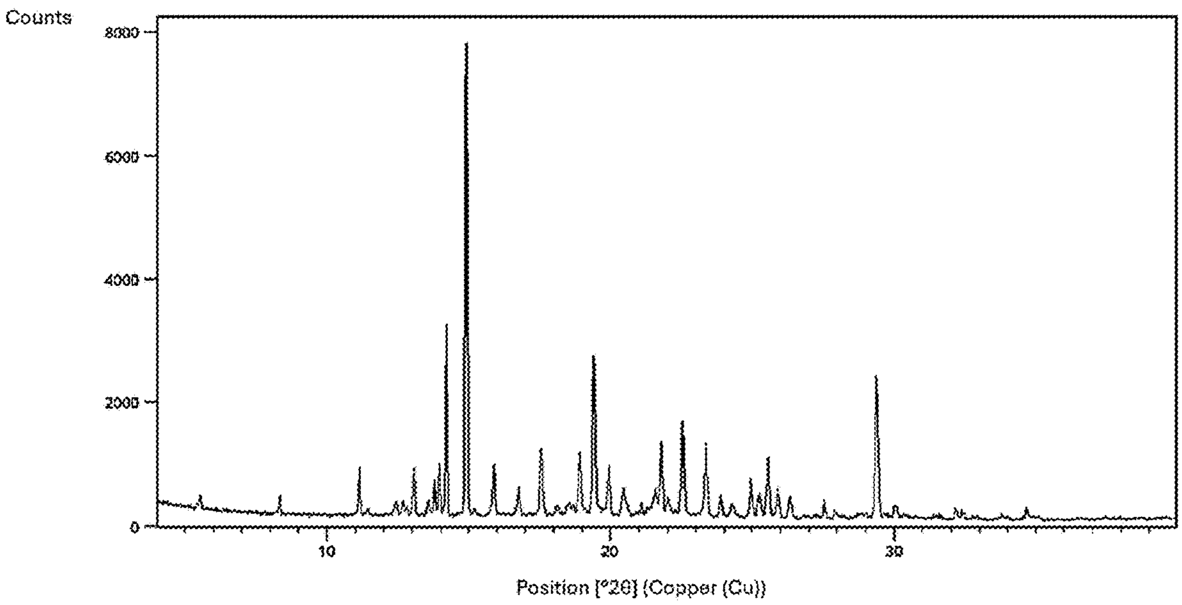
FIG. 9 shows an X-ray powder diffraction (XRPD) pattern of Form III of sabcomeline stearate prepared according to Example 7.

In another embodiment, the present invention comprises a crystalline form of sabcomeline stearate designated as Form I. The crystalline Form I of sabcomeline stearate is characterized by data selected from one or more of the following: an XRPD pattern substantially as featuring in Table 4; two, three, four, five, six, seven, eight, nine, ten or more 2θ±0.2° 2θ peaks as featuring in Table 4; or as depicted in FIG. 7; or as a combination thereof. In another embodiment, the present invention comprises a crystalline form of sabcomeline stearate designated as Form II. The crystalline Form II of sabcomeline stearate is characterized by data selected from one or more of the following: an XRPD pattern substantially as featuring in Table 5; two, three, four, five, six, seven, eight, nine, ten or more 2θ±0.2° 2θ peaks as featuring in Table 5; or as depicted in FIG. 8; or as a combination thereof. In another embodiment, the present invention comprises a crystalline form of sabcomeline stearate designated as Form III. The crystalline Form III of sabcomeline stearate is characterized by data selected from one or more of the following: an XRPD pattern substantially as featuring in Table 6; two, three, four, five, six, seven, eight, nine, ten or more 2θ±0.2° 2θ peaks as featuring in Table 6; or as depicted in FIG. 9; or as a combination thereof.

In one embodiment, the present invention comprises crystalline sabcomeline stearate exhibiting two, three, four or more of the following peaks, 11.1, 13.1, 13.9, 14.2, 14.9, 15.9, 17.5, 18.9, 19.4, 19.9, 21.8, 22.5, 23.3, 23.4, 25.0, 25.6, 29.4° 2θ±0.2° 2θ. In one embodiment, the present invention comprises crystalline sabcomeline stearate exhibiting at least peaks at 11.1, 14.2, 18.9, 19.4° 2θ±0.2° 2θ and optionally exhibit one, two, three, four, five, six, seven, eight, nine, ten or more of the following peaks, 13.1, 13.9, 14.9, 15.9, 17.5, 19.9, 21.8, 22.5, 23.3, 23.4, 25.0, 25.6, 29.4° 2θ±0.2° 2θ.

In one embodiment, the present invention comprises sabcomeline stearate and wherein less than 5% w/w of said crystalline sabcomeline stearate exhibits peaks at 15.8, 16.5, 18.8 and 22.3° 2θ±0.2° 2θ. In a further embodiment, the present invention comprises sabcomeline stearate and wherein less than 5% w/w; less than 4% w/w; less than 3% w/w; less than 2% w/w; less than 1% w/w or less than 0.5% w/w of said sabcomeline stearate exhibits peaks at 15.8, 16.5, 18.8 and 22.3° 2θ±0.2° 2θ. In a still further embodiment, the present invention comprises sabcomeline stearate which does not exhibit peaks at 15.8, 16.5, 18.8 and 22.3° 2θ±0.2° 2θ.

In one embodiment, the present invention comprises solid state sabcomeline stearate wherein the sabcomeline stearate comprises a single polymorphic form of sabcomeline. In other embodiments, the solid state sabcomeline stearate comprises two or more sabcomeline stearate polymorphic forms. In a further embodiment, the solid state sabcomeline stearate comprises about 50-100% Form III.

The present invention also encompasses the use of sabcomeline stearate, and solid-state forms thereof, for the preparation of compositions and pharmaceutical compositions.

While the compounds for use according to the invention may be administered in the form of the raw compound, it is preferred to introduce the active ingredient(s) in a pharmaceutical composition together with one or more adjuvants, excipients, carriers, buffers, diluents, and/or other pharmaceutical auxiliaries.

In one embodiment of the invention, the present invention encompasses pharmaceutical compositions comprising sabcomeline stearate and solid-state forms thereof.

In another embodiment, the present invention encompasses pharmaceutical compositions comprising sabcomeline stearate, and solid-state forms thereof, and at least one pharmaceutically acceptable excipient.

The excipient(s) must be "acceptable" in the sense of being compatible with the other ingredients of the formulation and not harmful to the recipient thereof.

Having described the disclosure with reference to certain preferred embodiments, other embodiments will become apparent to one skilled in the art from consideration of the specification. The disclosure is further illustrated by reference to the following examples describing in detail the preparation of the composition and methods of use of the disclosure. It will be apparent to those skilled in the art that many modifications, both to materials and methods, may be practiced without departing from the scope of the disclosure.

EXAMPLES

Example 1: Aqueous Solubility of Sabcomeline HCl

An excess amount of the sabcomeline HCl substance solid powder (Chemieliva biotech Co.) was added to HPLC glass vials (20-100 mg), and USP buffers at pH 1.6, 3, 5, 7, 9, and 11 were added (0.1-0.5 mL). Subsequently, the prepared samples were vortexed for 5 minutes, sonicated and stirred at 300 rpm at 25° C.

To chase the equilibrium solubility, any significant change in the pH of the buffer (i.e., >0.5 pH unit) was treated by adding acid (HCl) or base (NaOH) to get it back to the nominal value. In addition, any clear solution was treated by adding additional powder. The samples were stirred at 25° C. for 24 hours at 300 rpm. To remove any undissolved drug after the stirrer time, the samples were centrifuged for 15 minutes at 13,300 rpm speed. The supernatant was then removed and filtered via 0.2 μm centrifugal filter tubes. The obtained clear solutions were measured for pH and then diluted before HPLC injection.

XRPD analyses of the residual particles were performed using a Panalytical Empyrean diffractometer equipped with a Cu X-ray tube and a PIXcel 1D-Medipix3 detector system. The samples were analyzed at ambient temperature in transmission mode on a 96 well plate and held on mylar polymer film. XRPD patterns were sorted, manipulated, and indexed using HighScore Plus v4.9 software. The results of the solubility screen are described in Table 1 and demonstrate that according to USP definitions, sabcomeline HCl is considered to be freely water soluble (100-1000 mg/ml).

TABLE 2

| Buffer names | Solubility of sabcomeline HCl (mg/mL) | Solubility of sabcomeline HCl (w/w %) | Final pH |
|---|---|---|---|
| HCl buffer 1.6 | 654.7 | 56.582 | 1.8 |
| Acid Phthalate buffer 3.0 | 649.6 | 56.444 | 3.5 |
| Neutralized Phthalate buffer 5.0 | 658.7 | 56.855 | 5.0 |
| Phosphate buffer 7.0 | 657.5 | 57.081 | 6.9 |
| Alkaline Borate buffer 9.0 | 43.6 | 4.3 | 9.0 |
| Alkaline Borate buffer 11.0 | 10.5 | 1.0 | 11.2 |

Example 2: Hygroscopicity Study of Sabcomeline HCl

An empty vessel and stopper were weighted (M1). Sabcomeline HCl salt was placed in the vessel and closed by stopper and the vessel re-weighed (M2). The vessel was placed without the stopper in a desiccator for 24 hours at 25° C. and at 80±2% relative humidity (RH). The vessel was then removed from the desiccator, the stopper added directly to the vessel and the total weight rerecorded (M3). The percentage increase in the mass was calculated according to the following equation: $(M3-M2)/(M2-M1)\times 100$.

The material was found to undergo deliquescence, changing from a white powder to a transparent solid. The calculated increase in mass was found to be 33.8%, thereby classifying sabcomeline HCl under European Pharmacopoeia definitions as H-4 very hygroscopic (>15% increase in mass at 80% RH/24 hours).

Example 3: Synthesis of Sabcomeline Free Base 50 mg of sabcomeline HCl salt (Chemieliva biotech Co.) was weighed in a glass vial and dissolved in 40 μL of water. 35 mg of sodium carbonate was added to the solution and the resultant suspension vortexed until it mixed, after which it was allowed to evaporate to dryness and then dried further under vacuum overnight. 500 μL of methanol was then added to the resultant dried residue and stirred at ambient temperatures for 15 minutes. Solid residue was removed via centrifugal filtration and the filtrate transferred to a glass vial. The solids were washed with 200 μL of methanol and removed via centrifugal filtration. The combined filtrates were added together within a glass vial and died under nitrogen before being transferred to a vacuum desiccator for further drying overnight. The resultant oil was analyzed by proton NMR spectroscopy and the spectrum found to be consistent with that of sabcomeline free base.

Example 4: Synthesis of Sabcomeline Oxalate

Attempts to synthesize sabcomeline oxalate were undertaken with the resultant forms assayed by NMR and XRPD.

Example 4a: Synthesis of Sabcomeline Oxalate Form I 30 mg of sabcomeline free base was combined within a glass vial together with an equimolar amount of 0.1M oxalic acid aqueous stock solution, mixed and stirred with a magnetic stirrer at ambient temperature. No precipitation was observed after two days, following which the vial was uncapped and left to evaporate at ambient temperature to yield a solid precipitate. The precipitate was isolated and NMR analysis of the isolate confirmed the compound to be sabcomeline oxalate. XRPD analysis of the isolated salt identified it as sabcomeline oxalate Form I and showed it to be crystalline with the XRPD pattern as shown in FIG. 1.

Figure 2:
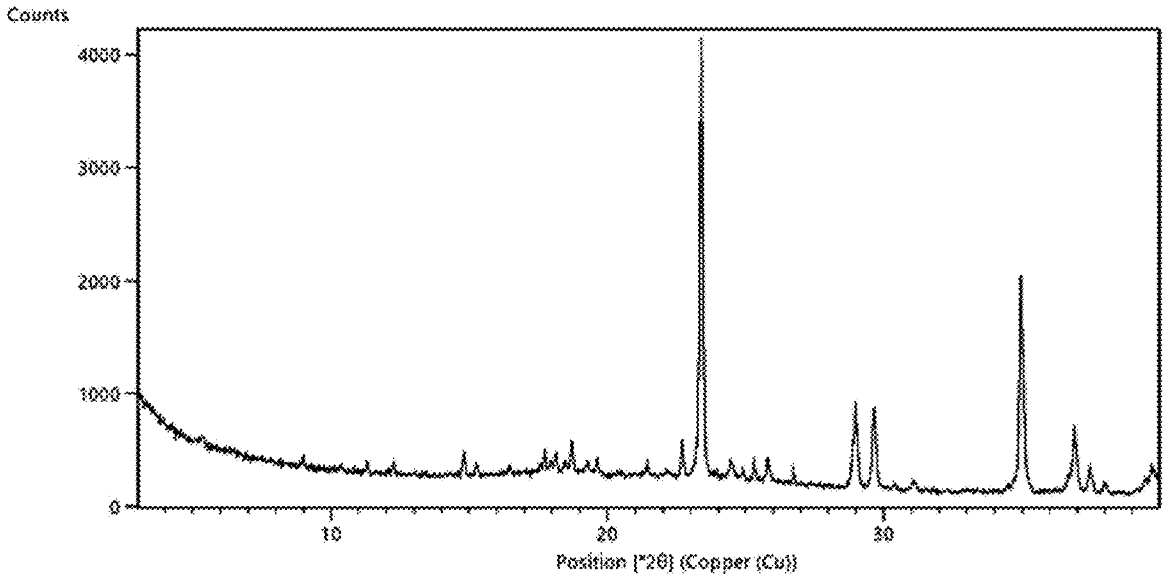
FIG. 2 shows an X-ray powder diffraction (XRPD) pattern of Form II of sabcomeline oxalate prepared according to Example 4b.

Example 4b: Synthesis of Sabcomeline Oxalate Form II 25 mg of sabcomeline free base was combined within a glass vial together with an excess amount of 0.1M oxalic acid aqueous stock solution. The resultant solution was evaporated in a dessicator under vacuum to yield a solid precipitate. The precipitate was isolated and NMR analysis of the isolate confirmed the compound to be sabcomeline oxalate. XRPD analysis of the isolated salt identified it as sabcomeline oxalate Form II and showed it to be crystalline with the XRPD pattern as shown in FIG. 2.

Figure 3:
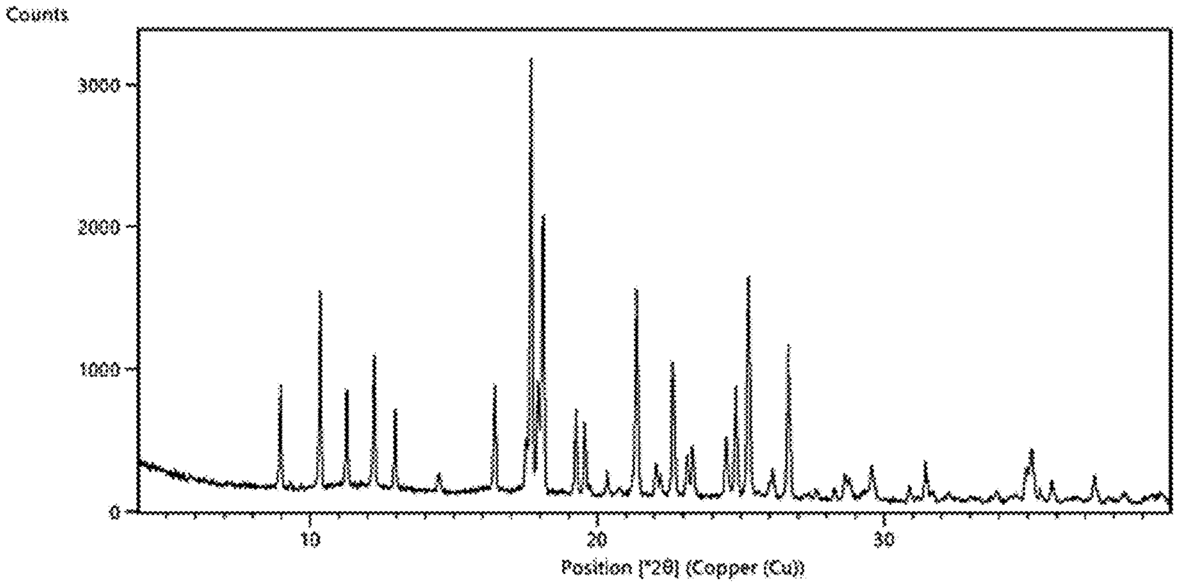
FIG. 3 shows an X-ray powder diffraction (XRPD) pattern of Form III of sabcomeline oxalate prepared according to Example 4c.

Example 4c: Synthesis of Sabcomeline Oxalate Form III 30 mg of sabcomeline free base was combined within a glass vial together with a twice equimolar amount of 0.1M oxalic acid stock solution, mixed and stirred with a magnetic stirrer at ambient temperature. No precipitation was observed after two days, following which the vial was uncapped and left to evaporate at ambient temperature. As no precipitate was observed following the evaporation, the dried residue was slurried at room temperature in methanol to yield a solid precipitate. The precipitate was isolated and NMR analysis of the isolate confirmed the compound to be sabcomeline oxalate. XRPD analysis of the isolated salt identified it as sabcomeline oxalate Form III and showed it to be crystalline with the XRPD pattern as shown in FIG. 3.

Figure 4:
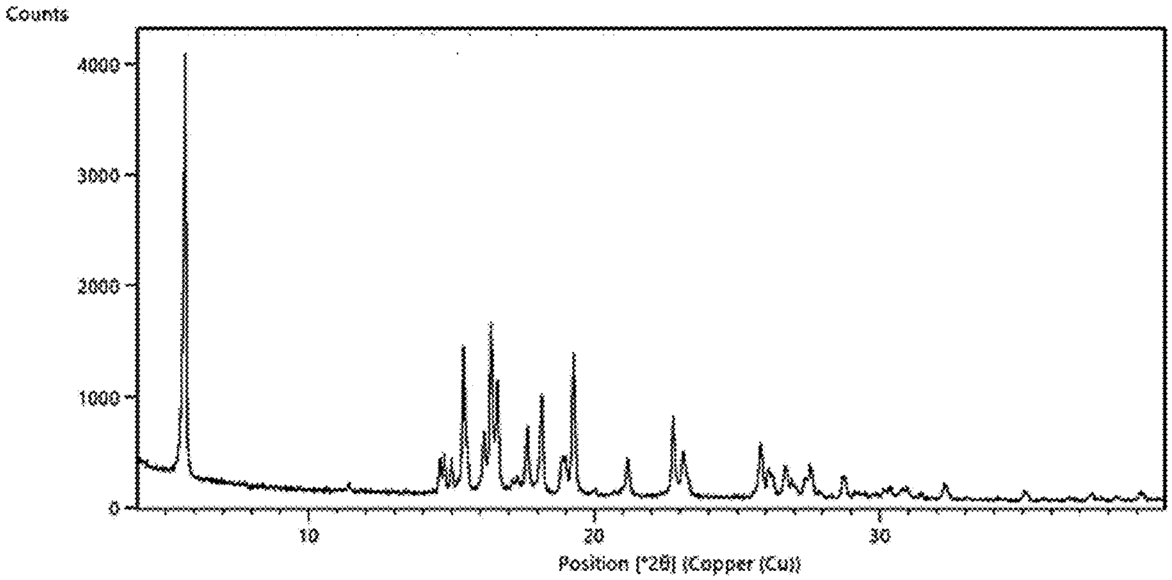
FIG. 4 shows an X-ray powder diffraction (XRPD) pattern of Form IV of sabcomeline oxalate prepared according to Example 4d.

Example 4d: Synthesis of Sabcomeline Oxalate Form IV 30 mg of sabcomeline free base was combined within a glass vial together with 0.5 mol equivalent of 0.1M oxalic acid stock solution and THE, mixed and stirred with a magnetic stirrer at ambient temperature overnight to yield a solid precipitate. The precipitate was isolated and NMR analysis of the isolate confirmed the compound to be sabcomeline oxalate. XRPD analysis of the isolated salt identified it as sabcomeline oxalate Form IV and showed it to be crystalline with the XRPD pattern as shown in FIG. 4.

Example 4e: Synthesis of Sabcomeline Oxalate Form III+V (1:1 Methanol:Acetone)

Figure 5:
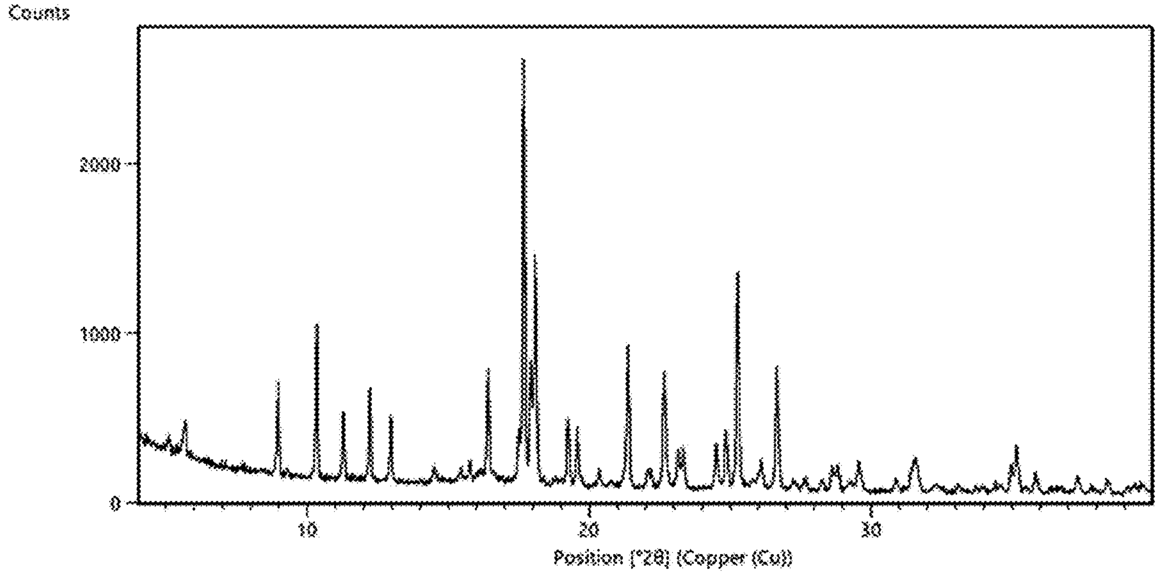
FIG. 5 shows an X-ray powder diffraction (XRPD) pattern of Form III+V of sabcomeline oxalate prepared according to Example 4e.

30 mg of sabcomeline free base was combined within a glass vial together with an equimolar amount of 0.1M oxalic acid stock solution and 250 μL of 1:1 methanol:acetone, mixed and stirred with a magnetic stirrer on a hot plate at 40° C. until dissolution was observed to occur, following which the sample was left to cool to yield a solid precipitate which was isolated. XRPD analysis of the isolated salt identified it as a mixture of sabcomeline oxalate Form III and Form V and showed it to be crystalline with the XRPD pattern as shown in FIG. 5.

Example 4f: Synthesis of Sabcomeline Oxalate Forms I+IV (1:1 Methanol:Acetone)

30 mg of sabcomeline free base was combined within a glass vial together with an equimolar amount of 0.1M oxalic acid stock solution and 250 μL of 1:1 methanol:acetone, mixed and stirred with a magnetic stirrer for 2 days, following which the vial was uncapped and allowed to evaporate in a fume hood at ambient temperature to yield a solid precipitate which was isolated. XRPD analysis of the isolated salt identified it as a mixture of sabcomeline oxalate Form I and Form IV and showed it to be crystalline.

Example 4g: Synthesis of Sabcomeline Oxalate Forms I+III (3:1 Methanol:Acetone)

30 mg of sabcomeline free base was combined within a glass vial together with an equimolar amount of 0.1M oxalic acid stock solution and 250 μL of 3:1 methanol:acetone, mixed and stirred with a magnetic stirrer at ambient temperature for 2 days to yield a solid precipitate, following which the sample was left to cool to yield a solid precipitate which was isolated. XRPD analysis of the isolated salt identified it as a mixture of sabcomeline oxalate Form I and Form III and showed it to be crystalline.

Example 4h: Synthesis of Sabcomeline Oxalate Forms I+VI (1:3 Methanol:Acetone)

Figure 6:
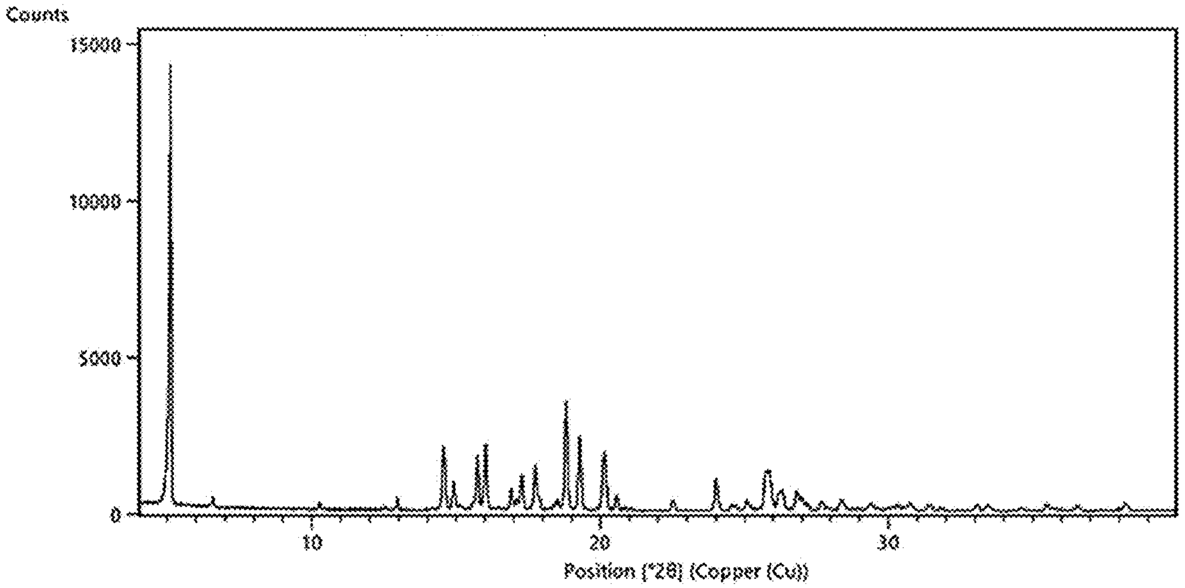
FIG. 6 shows an X-ray powder diffraction (XRPD) pattern of Form I+VI of sabcomeline oxalate prepared according to Example 4h.

285 mg of sabcomeline free base was combined within a glass vial together with an equimolar amount of 0.1M oxalic acid stock solution and 1.2 mL of 1:3 methanol:acetone and the suspension was slurried overnight to yield a solid precipitate. The precipitate was isolated and NMR analysis of the isolate confirmed the compound to be sabcomeline oxalate. XRPD analysis of the isolated salt identified it as a mixture of sabcomeline oxalate Form I and Form VI and showed it to be crystalline with the XRPD pattern as shown in FIG. 6.

Example 4i: Melting Temperature Range Analysis of Sabcomeline Oxalate

The melting temperature range of the forms of sabcomeline oxalate, as prepared according to Examples 1a-h, were each identified using TG/DTA and the results shown in Table 2.

TABLE 2

| Sabcomeline salt form | Melting Temperature Range (° C.) |
|---|---|
| Oxalate salt Type I | 148-156 |
| Oxalate salt Type II | 85-97 |
| Oxalate salt Type III | 160-168 |
| Oxalate salt Type IV | 192-198 |
| Oxalate salt Type I + VI | 150-155 |

Three small samples of the compound of Example 4h were also placed into glass capillaries, introduced into a Büchi B-545 Melting Point Apparatus and heated at a constant ramp rate of 1° C./min. The range of melting points, as recorded by visual observation, was 152.4-152.7° C.

Example 4j: Aqueous Solubility of Sabcomeline Oxalate

The aqueous solubility of sabcomeline oxalate Forms I-IV and I+VI were each estimated via the aliquot addition method. A weighed aliquot of about 10 mg of each form of sabcomeline oxalate were added to glass vials and aliquots of water added until dissolution was observed. The first 100 μL was added in 20 μL aliquots. The volume was made up to 200 μL in 50 μL aliquots, and the volume was made up to 1 mL in 100 μL aliquots with the aqueous solubility of the salt forms determined as shown in Table 3. The results of the solubility screen demonstrate that according to USP definitions, sabcomeline oxalate is considered to be freely water soluble (100-1000 mg/ml).

TABLE 3

| Sabcomeline salt form | Solubility Range (mg/mL) |
|---|---|
| Oxalate salt Type I | 290-580 |
| Oxalate salt Type II | 97-145 |
| Oxalate salt Type III | 145-193 |
| Oxalate salt Type IV | >502 |
| Oxalate salt Type I + VI | 61-122 |

Example 5: Synthesis of Sabcomeline Stearate (20 mg Scale)

A 0.1M solution of 20 mg of sabcomeline free base was combined within a glass vial together with an equimolar amount of stearic acid and stirred over night with a magnetic stirrer at ambient temperature in an excess of THE, following which precipitation was observed. The precipitate was isolated. NMR analysis of the isolate confirmed the compound to be sabcomeline monostearate.

XRPD analyses of the residual particles were performed using a Panalytical Empyrean diffractometer equipped with a Cu X-ray tube and a PIXcel 1D-Medipix3 detector system. The samples were analyzed at ambient temperature in transmission mode and held on polymer films. XRPD patterns were sorted, manipulated, and indexed using HighScore Plus v4.9 software. XRPD analysis of the isolated stearate salt identified it as sabcomeline stearate Form I and showed it to be highly crystalline with the XRPD pattern as shown in FIG. 7 and as having peaks as reported in Table 4.

TABLE 4

| Position (°) | Intensity (CPS) | Relative Intensity (%) |
|---|---|---|
| 4.1 | 97.0 | 5.8 |
| 4.7 | 275.6 | 16.5 |
| 4.8 | 1522.7 | 91.0 |
| 5.5 | 109.0 | 6.5 |
| 9.6 | 316.5 | 18.9 |
| 14.2 | 104.2 | 6.2 |
| 14.4 | 1476.5 | 88.2 |
| 14.7 | 125.4 | 7.5 |
| 14.8 | 79.8 | 4.8 |
| 15.0 | 196.4 | 11.7 |
| 15.2 | 216.9 | 13.0 |
| 15.8 | 92.5 | 5.5 |
| 15.8 | 686.2 | 41.0 |
| 16.0 | 309.1 | 18.5 |
| 16.2 | 474.4 | 28.4 |
| 16.5 | 687.4 | 41.1 |
| 17.2 | 209.4 | 12.5 |
| 17.4 | 500.5 | 29.9 |
| 17.8 | 93.7 | 5.6 |
| 18.3 | 37.5 | 2.2 |
| 18.5 | 92.8 | 5.6 |
| 18.6 | 384.5 | 23.0 |
| 18.8 | 637.6 | 38.1 |
| 19.3 | 224.6 | 13.4 |
| 19.9 | 45.2 | 2.7 |
| 20.1 | 431.3 | 25.8 |

TABLE 4-continued

| Position (°) | Intensity (CPS) | Relative Intensity (%) |
|---|---|---|
| 20.3 | 1423.0 | 85.0 |
| 20.5 | 1001.3 | 59.8 |
| 21.4 | 181.5 | 10.9 |
| 22.1 | 778.4 | 46.5 |
| 22.3 | 559.8 | 33.5 |
| 22.7 | 126.9 | 7.6 |
| 23.0 | 45.0 | 2.7 |
| 23.2 | 32.0 | 1.9 |
| 23.6 | 168.0 | 10.0 |
| 24.0 | 1673.7 | 100.0 |
| 24.5 | 183.8 | 11.0 |
| 25.1 | 181.7 | 10.9 |
| 26.0 | 39.4 | 2.4 |
| 26.9 | 8.9 | 0.5 |
| 27.0 | 130.2 | 7.8 |
| 28.2 | 9.0 | 0.5 |
| 28.7 | 121.9 | 7.3 |
| 29.2 | 87.1 | 5.2 |
| 29.6 | 120.1 | 7.2 |
| 31.1 | 36.7 | 2.2 |
| 33.3 | 24.8 | 1.5 |
| 39.8 | 17.6 | 1.1 |

Example 6: Synthesis of Sabcomeline Stearate (100 mg Scale)

100 mg of sabcomeline free base together with an equimolar amount of stearic acid were weighed into a vial. 666 μL of THF was added and the suspension stirred at ambient temperature overnight producing a cloudy suspension. This suspension was then seeded with sabcomeline stearate Form I and stirred together for a further five days. Solids precipitated from the suspension and were isolated via centrifugation and decantation followed by air drying. NMR analysis of the isolate confirmed the compound to be sabcomeline monostearate.

XRPD analyses of the residual particles were performed using a Panalytical Empyrean diffractometer equipped with a Cu X-ray tube and a PIXcel 1D-Medipix3 detector system. The samples were analyzed at ambient temperature in transmission mode and held on polymer films. XRPD patterns were sorted, manipulated, and indexed using HighScore Plus v4.9 software. XRPD analysis of the isolated stearate salt identified it as sabcomeline stearate Form II and showed it to be crystalline with the XRPD pattern having peaks as shown in FIG. 8 and as reported in Table 5.

TABLE 5

| Position (°) | Intensity (CPS) | Relative Intensity (%) |
|---|---|---|
| 5.5 | 347.5 | 0.9 |
| 7.4 | 10.2 | 0.0 |
| 9.3 | 110.6 | 0.3 |
| 11.4 | 3459.6 | 9.3 |
| 12.8 | 37340.0 | 100.0 |
| 13.1 | 95.4 | 0.3 |
| 14.8 | 257.4 | 0.7 |
| 16.0 | 49.8 | 0.1 |
| 16.3 | 469.8 | 1.3 |
| 16.7 | 253.8 | 0.7 |
| 17.0 | 601.2 | 1.6 |
| 17.1 | 2668.7 | 7.2 |
| 17.9 | 1602.0 | 4.3 |
| 18.2 | 997.6 | 2.7 |
| 18.6 | 1173.6 | 3.1 |
| 19.4 | 138.6 | 0.4 |
| 19.7 | 146.0 | 0.4 |
| 20.1 | 865.5 | 2.3 |
| 20.7 | 103.4 | 0.3 |

TABLE 5-continued

| Position (°) | Intensity (CPS) | Relative Intensity (%) |
|---|---|---|
| 21.3 | 10683.1 | 28.6 |
| 21.5 | 157.9 | 0.4 |
| 22.0 | 4698.1 | 12.6 |
| 22.2 | 1702.0 | 4.6 |
| 22.7 | 175.4 | 0.5 |
| 23.0 | 594.6 | 1.6 |
| 23.6 | 441.9 | 1.2 |
| 23.9 | 289.2 | 0.8 |
| 25.7 | 247.6 | 0.7 |
| 25.8 | 800.7 | 2.1 |
| 26.3 | 197.5 | 0.5 |
| 27.3 | 433.7 | 1.2 |
| 27.5 | 2585.6 | 6.9 |
| 28.7 | 160.1 | 0.4 |
| 28.8 | 67.3 | 0.2 |
| 29.8 | 426.0 | 1.1 |
| 30.0 | 171.8 | 0.5 |
| 30.3 | 405.4 | 1.1 |
| 30.7 | 73.8 | 0.2 |
| 31.2 | 98.1 | 0.3 |
| 32.3 | 32.3 | 0.1 |
| 32.9 | 86.3 | 0.2 |
| 34.0 | 70.9 | 0.2 |
| 34.5 | 53.4 | 0.1 |
| 34.7 | 65.9 | 0.2 |
| 35.0 | 42.7 | 0.1 |
| 35.3 | 44.6 | 0.1 |
| 36.3 | 31.1 | 0.1 |
| 37.1 | 63.3 | 0.2 |
| 38.1 | 30.8 | 0.1 |
| 39.1 | 262.8 | 0.7 |
| 39.7 | 69.1 | 0.2 |

Example 7: Synthesis of Sabcomeline Stearate (300 mg Scale)

300 mg of sabcomeline free base together with an equimolar amount of stearic acid were weighed into a vial. 1998 μL μL of THF was added and the suspension stirred overnight. The suspension dissolved forming a solution to which seeds of sabcomeline Form I were added and the mixture stirred overnight. The resultant solution became cloudy without observable precipitation. The solution was evaporated under a stream of $N_2$ and additional seeds added with the resultant, concentrated solution stirred at ambient temperatures for four days after which the vial was uncapped, the solution allowed to evaporate and a gel recovered which was stirred in 400 μL of heptane for five days following which solid material precipitated. NMR analysis of the material confirmed the compound to be sabcomeline monostearate.

XRPD analyses of the residual particles were performed using a Panalytical Empyrean diffractometer equipped with a Cu X-ray tube and a PIXcel 1D-Medipix3 detector system. The samples were analyzed at ambient temperature in transmission mode and held on polymer films. XRPD patterns were sorted, manipulated, and indexed using HighScore Plus v4.9 software. XRPD analysis of the isolated stearate salt identified it as sabcomeline stearate Form III and showed it to be crystalline with the XRPD pattern having peaks as shown in FIG. 9 and as reported in Table 6.

TABLE 6

| Position (°) | Intensity (CPS) | Relative Intensity (%) |
|---|---|---|
| 5.5 | 48.6 | 0.7 |
| 5.5 | 139.3 | 1.9 |

TABLE 6-continued

| Position (°) | Intensity (CPS) | Relative Intensity (%) |
|---|---|---|
| 8.3 | 176.8 | 2.4 |
| 11.1 | 599.7 | 8.3 |
| 11.4 | 82.9 | 1.1 |
| 12.4 | 160.2 | 2.2 |
| 12.7 | 173.8 | 2.4 |
| 12.8 | 98.0 | 1.4 |
| 13.1 | 626.4 | 8.6 |
| 13.6 | 171.7 | 2.4 |
| 13.8 | 489.9 | 6.8 |
| 13.9 | 703.5 | 9.7 |
| 14.2 | 2810.3 | 38.7 |
| 14.9 | 7259.8 | 100.0 |
| 15.2 | 72.1 | 1.0 |
| 15.9 | 671.9 | 9.3 |
| 16.7 | 340.5 | 4.7 |
| 17.1 | 32.3 | 0.5 |
| 17.5 | 867.4 | 12.0 |
| 18.1 | 126.7 | 1.7 |
| 18.5 | 143.4 | 2.0 |
| 18.7 | 99.0 | 1.4 |
| 18.9 | 847.1 | 11.7 |
| 19.4 | 2091.6 | 28.8 |
| 19.7 | 71.8 | 1.0 |
| 19.9 | 567.7 | 7.8 |
| 20.5 | 410.0 | 5.7 |
| 21.1 | 89.9 | 1.2 |
| 21.6 | 263.6 | 3.6 |
| 21.6 | 49.2 | 0.7 |
| 21.8 | 851.5 | 11.7 |
| 22.0 | 199.7 | 2.8 |
| 22.5 | 1161.9 | 16.0 |
| 23.3 | 599.7 | 8.3 |
| 23.4 | 760.9 | 10.5 |
| 23.9 | 244.0 | 3.4 |
| 24.3 | 172.7 | 2.4 |
| 25.0 | 582.3 | 8.0 |
| 25.2 | 320.2 | 4.4 |
| 25.3 | 230.8 | 3.2 |
| 25.5 | 304.1 | 4.2 |
| 25.6 | 787.1 | 10.8 |
| 25.8 | 32.1 | 0.4 |
| 25.9 | 441.7 | 6.1 |
| 26.3 | 260.7 | 3.6 |
| 26.9 | 23.1 | 0.3 |
| 27.5 | 259.0 | 3.6 |
| 27.9 | 147.5 | 2.0 |
| 28.8 | 50.4 | 0.7 |
| 29.4 | 2234.6 | 30.8 |
| 30.0 | 175.0 | 2.4 |
| 31.5 | 47.8 | 0.7 |
| 32.2 | 143.1 | 2.0 |
| 32.3 | 13.2 | 0.2 |
| 32.4 | 150.3 | 2.1 |
| 32.8 | 31.2 | 0.4 |
| 33.8 | 71.7 | 1.0 |
| 34.6 | 151.8 | 2.1 |

Example 8: Aqueous Solubility of Sabcomeline Stearate

The aqueous solubility of sabcomeline stearate Form I was estimated via the aliquot addition method. A weighed aliquot of 9.4 mg of sabcomeline stearate was added to a glass vial and aliquots of water added until dissolution was observed. The first 100 μL was added in 20 μL aliquots. The volume was made up to 200 μL in 50 μL aliquots, and the volume was made up to 1 mL in 100 μL aliquots with the aqueous solubility of the salt determined to be <9 mg/mL.

Example 9: Solvent Solubility of Sabcomeline Stearate

Example 9a: Aliquot Method

The solubility of sabcomeline stearate Form III in a variety of solvents was estimated via the aliquot addition method. A weighed aliquot of 10-20 mg of sabcomeline stearate was added to a virgin glass vial and aliquots of solvent added until dissolution was observed. The first 100 μL was added in in 20 μL aliquots. The volume was made up to 200 μL in 50 μL aliquots, and the volume was made up to 1 mL in 100 μL aliquots. The results of the solubility screen are shown in Table 7.

TABLE 7

| Solvent | Solubility Range (mg/mL) |
|---|---|
| Water | <17 |
| Dimethyl Sulfoxide (DMSO) | 13-14 |
| Dichloromethane (DCM) | 270-540 |
| Ethyl Acetate (EtOAc) | 283-565 |
| N-Methyl-2-2-Pyrrolidone (NMP) | 160-240 |
| triacetin | <13 |
| benzyl benzoate | 19-24 |
| formamide | <9 |

Example 9b: HPLC Method 50 mg of sabcomeline stearate was transferred into a 20 mL vial to which 5 mL of water was then added. The resultant solution was shaken at 37° C. in water bath and sampled by HPLC at 24 hours to assay the salt's solubility. The results of the solubility screen identified the solubility of sabcomeline stearate to be 9.4 mg/ml, demonstrating that according to USP definitions, the salt is considered to be only slightly soluble (1-10 mg/ml).

Example 10: Hygroscopicity Study of Sabcomeline Stearate

The hygroscopicity of about 40 mg of sabcomeline stearate Form III was assayed according to the methods described in Sihorkar et al (Pharmaceutical Dev. & Technol. (2013), 18 (2), 348-358) as a step profile of 10% increments from 40 to 90% relative humidity followed by desorption from 90 to 0% relative humidity and a second sorption cycle from 0 to 40% relative humidity. The weight change was monitored during the sorption cycle by Dynamic Vapour Sorption (DVS). Sabcomeline stearate Form III was found to increase in weight 0.61% thereby classifying the salt under European Pharmacopoeia definitions as H-2 slightly hygroscopic (≥0.2% but <2% increase in mass at 80% RH/24 hours).

The invention described herein may be practiced in the absence of any element or limitation which is not specifically disclosed herein. Thus, for example, in each instance herein, any of the terms "comprising," "consisting essentially of" and "consisting of" may be replaced with either of the other two terms. The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A crystalline sabcomeline stearate wherein the crystalline sabcomeline stearate exhibits X-ray powder diffraction (XRPD) pattern 2θ peaks at 14.2±0.2, 19.4±0.2 and 21.8±0.2.

2. A pharmaceutical composition comprising the crystalline sabcomeline stearate of claim 1 and at least one pharmaceutically acceptable excipient.

3. The pharmaceutical composition of claim 2, wherein the crystalline sabcomeline is present in the composition as a single polymorphic form.

4. The pharmaceutical composition of claim 2, wherein the crystalline sabcomeline is present in the composition as a mixture of two or more polymorphic forms.

* * * * *